United States Patent [19]

Schinitsky

[11] 4,208,414

[45] Jun. 17, 1980

[54] VINBLASTINE IN RHEUMATOID ARTHRITIS

[75] Inventor: Michael R. Schinitsky, Indianapolis, Ind.

[73] Assignee: Eli Lilly and Company, Indianapolis, Ind.

[21] Appl. No.: 39,078

[22] Filed: May 14, 1979

Related U.S. Application Data

[63] Continuation-in-part of Ser. No. 912,672, Jun. 5, 1978, abandoned.

[51] Int. Cl.² ............................................ A61K 31/475
[52] U.S. Cl. .................................................... 424/262
[58] Field of Search ................................. 424/262, 195

[56] References Cited

PUBLICATIONS

T. Y. Shen, Drug in Experimental Clin. Res. (1977), vol. II(I), pp. 1–8.
Abstract of 14th International Cong. Rheumatism Abst. 428 & 661, 6-26-77.
Phelps et al., J. Exp. Med. 124 145 (1966).
Chang et al. Arthritis & Rheumatism, vol. XI, No. 2, Part 1, Apr. 1968, pp. 145–150.
Floresheim et al., Agents & Actions, vol. 3/1 (1973), pp. 24–27.
Fitzgerald et al., Pharmacology, 6:265–273 (1971).

*Primary Examiner*—Stanley J. Friedman
*Attorney, Agent, or Firm*—James L. Rowe; Arthur R. Whale

[57] ABSTRACT

Vinblastine (vincaleucoblastine, VLB) and other antimitotic vinca alkaloid is useful in the treatment of rheumatoid arthritis and related diseases, alone or in combination with an anti-inflammatory agent.

13 Claims, No Drawings

VINBLASTINE IN RHEUMATOID ARTHRITIS

CONTINUING DATA

This is a continuation in part of Ser. No. 912,672, filed June 5, 1978 and now abandoned.

BACKGROUND OF THE INVENTION

Vinblastine (U.S. Pat. No. 3,097,137) has been employed for a number of years as an oncolytic agent particularly useful in the treatment of Hodgkin's Disease and other lymphomas. It is generally administered by the intravenous route to patients suffering from one of these diseases. There has been a sparse amount of research work reported involving vinblastine, or other oncolytic vinca alkaloids and their derivatives, directed toward their physiological action in non-neoplastic conditions. For example, vinblastine has been used to induce leucopenia in experimental animals and the effect of that leucopenia on other conditions studied. Phelps and McCarty, writing in *J. Exp. Med.*, 124 115 (1966), induced a gouty arthritis type of inflammation in dogs by the injection into the joint of microcrystalline sodium urate. An acute inflammatory reaction was ordinarily produced, but, in dogs pretreated with vinblastine at such a dose level that there was a profound leukocyte depletion, significant phagocyte accumulation was prevented and the inflammatory response was almost completely abolished. This finding led the authors to the conclusion that, in the particular experimental model, the polymorphonuclealeukocyte was necessary to the urate-crystal induced inflammation. Chang and Gralla, writing in *Arthritis and Rheumatism*, 11, 145 (1968), investigated the possibility that the effects of vinblastine on joint inflammation found by Phelps and McCarty were mediated by means other than the reduction in the number of polymorphs. These authors produced a leucopenia in dogs by using rabbit-anti-dog-polymorphonuclear serum. It was their conclusion that their findings were in accord with those of Phelps and McCarthy as regards the role of a vinblastine-induced leucopenia in preventing inflammation subsequent to the injection of mycrocrystalline urate into canine joints. Floresheim, et al. writing in *Agents and Actions*, 3 24 (1973) induced an acute arthritis in pigeons or chickens by the injection of microcrystalline sodium urate into the intertarsal joint. They found no inhibition of the arthritic response from a number of agents including both vinblastine and vincristine. Fitsgerald, et al., *Pharmacology*, 6, 265 (1971) used a different model—the sodium urate-induced paw swelling in mice. The authors found that various anti-mitotics including vinblastine and vincristine produced a significant depression of paw swelling at similar dose levels. The effects of the various anti-mitotic agents did not seem to bear any relation to their anti-mitotic potency. T. Y. Shen, in an article titled "The Expanding Vistas of Non-acidic Anti-arthritic Agents" in *Drugs in Experimental Clinical Research* Vol II (1) (1977) speculates that one approach, among many, for regulation of the immuno-pathology of arthritis would be to investigate the effect of selective membrane modulators upon this disease. According to Shen, "[p]hagocytosis and the function of membrane receptors and enzymes are subject to the regulation by the fluidity of the bi-layer membrane by the submembrane structures, microtubules and microfilaments . . . ." He reports that among the classical inhibitors of microtubules are included the vinca alkaloids, vinblastine and vincristine, the anti-tumor drug, maytensine, phodphyllotoxin and colchicin. Finally, in June, 1977, a question was raised as to whether it would be useful to use vinblastine in the treatment of systemic sclerosis (Abstracts of the 14th International Congress of Rheumatism—June 26, 1977, San Francisco, California—Abstract No. 661). The authors concluded that it would be. At the same meeting, a paper was presented (Abstract No. 426) concerning the effect of the intravenous administration of vinblastine on inflammation induced by the injection of pulverized calcium pyrophosphate dihydrate crystals into the pleural cavity. The authors concluded that vinblastine may have a suppressive effect on the inflammation thus induced.

SUMMARY OF THE INVENTION

This invention provides a method of treating rheumatoid arthritis which comprises administering to a mammal suffering from rheumatoid arthritis and in need of treatment, an amount of a vinca-derived oncolytic agent, specifically vinblastine, effective to arrest the progress of the disease. Administration can be parenteral, specifically by the intrevenous route, or, preferably, oral. The amount of vinblastine administered varies according to the route employed. For example, by the intravenous route, a dose of 0.1 to 0.5 mg./kg. can be employed (3.7 to 18.5 mg. per meter squared), whereas the oral dosage would be roughly ten times as great (1 to 5 mg./kg.). The drug is customarily administered once (as contrasted with the daily, every third day, or weekly dosage regimen when vinblastine is used to treat Hodgkin's Disease or related neoplasms). If required, the dosage can be repeated, but not more often than every two weeks or once a month in order to avoid cumulative side-effects.

In a second aspect of this invention, vinblastine is administered in conjunction with an anti-inflammatory agent of the profen class including ibuprofen, ($\pm$) $\alpha$-methyl-4-(2-methylpropyl)benzeneacetic acid; carprofen, $\alpha$-methyl-6-chlorocarbazole-2-acetic acid; cicloprofen, $\alpha$-dl-2-methylfluorene-2-acetic acid; fenoprofen, dl-$\alpha$-methyl-3-phenoxybenzeneacetic acid; indoprofen, $\alpha$-methyl-4-(1,3-dihydro-1-oxo-2H-isoindolyl-2-yl)benzenacetic acid; ketoprofen, $\alpha$-methyl-3-benzoylbenzeneacetic acid; naproxyn, ($\pm$) $\alpha$-methyl-6-methoxy-2-naphthaleneacetic acid; pirprofen, dl-$\alpha$-methyl-3-chloro-4-(3-pyrrolidinol-1-yl)benzeneacetic acid; suprofen, dl-$\alpha$-methyl-4-(thienylcarbonyl)-benzeneacetic acid and benoxoprofen, dl-$\alpha$-methyl-2-(p-chlorophenyl)benzoxazoleacetic acid and the like drugs. Other non-profen type anti-inflammatory drugs such as indomethacin can also be used advantageously with VLB and like drugs to treat rheumatoid arthritis. Such combinations of drugs, a vinca alkaloid and an anti-inflammatory agent, are particularly valuable because the primary effect of vinblastine and related alkaloids is to arrest further progress of the rheumatoid process and administration of the drug afords little if any symptomatic relief whereas, by contrast, the chief effect of the anti-inflammatory drug is to alleviate the arthritic symptoms but with little or no hindrance to the progress of the arthritic process.

In the above therapeutic process, other vinca-derived oncolytic agents that can be employed include vindesine (C-3 carboxamide of 4-desacetyl vinblastine), vincristine, 4'-deoxyleurosidine, 1-formyl-4'-deoxyleurosidine (from U.S. Pat. No. 4,143,041) leuroformine, other amides from Cullinan and Gerzon, Ser. No. 828,693, filed Aug. 29, 1977, now copending, and the like. I prefer, however, to employ the orally-active vinca alkaloids, particularly VLB or a 4'-desacetyl VLB 3-spiro-5''-oxazolidine-2'',4''-dione permissibly substituted at C-3'' by methyl, 2-chloroethyl or the like groups, as disclosed by Miller and Gutowski, U.S. Pat. No. 4,096,148. These oxazolidinedione derivatives are equally active and less toxin than vinblastine when administered by the oral route. However, the dosage of other vinca alkaloid or alkaloid derivative to be administered, whether orally or parenterally, is a dosage equivalent to the dose of vinblastine in the ranges stated above.

For parenteral administration, vinblastine is administered in the form of its sulfate salt as an isotonic solution with a concentration on the order of 1 mg./ml. For oral administration, a tablet formulation is conveniently employed containing 10–100 mg. of vinblastine per tablet. Excipients employed in such tablets include lactose, anhydrous dicalcium phosphate, starch, etc. Lubricants such as magnesium stearate or stearic acid are also used. A typical useful tablet contains 50 mg. vinblastine sulfate, 500 mg. lactose, 500 mg. milk sugar, 100 mg. starch powder, 100 mg. anhydrous dicalcium phosphate, 10 mg. magnesium stearate, 25 mg. stearic acid and 50 mg. of a high molecular weight carboxy vinyl polymer (carbopol 934, B. F. Goodrich Chemical Company). The above ingredients are mixed in bulk and compressed into tablets such that each tablet contains the quantity of ingredient specified above. The tablets may be scored so that divided (one-half or one-quarter) doses can be administered.

If sulfate salts of other vinca alkaloids are to be employed, the amount of active drug present will vary according to the ratio of antiarthritic activity of the drug to that of vinblastine; for example, with parenteral administration, vincristine would be present in an ampoule for mixing with an isotonic solution at a 0.1 mg./ml. level since it is about 10 times more active than VLB. Orally, one of the aforementioned spirooxazolidinedione derivatives would be present in about the same concentration as that utilized for vinblastine, although higher doses of these newer derivatives can be administered because of their lowered toxicity and lessened side-effects.

As evidence of the activity of vinblastine in treating rheumatoid arthritis, the compound was subjected to an adjuvant-induced arthritis assay in rats. The assay was carried out as follows: female Wistar-Lewis rats weighing 200–220 gms. each were injected in the right hind paw with 0.25 mg. of heat-killed lyophilized *Mycyobacterium tuberculosis* sonicated and suspended in 0.05 ml. of heavy mineral oil. The injection was subplantar and induced arthritis in the paw of the rats. Vinblastine at various dose levels was administered on the 10th day after the subplantar injection and the average increase in swelling in the injected paw occuring pre and post-drug administration was measured and compared with the swelling in the uninjected paw. A saline control was also utilized. Table 1 which follows, gives the results of one such determination in Section A. In the table, column 1 gives the name of the drug, column 2, the dose level in mg./kg., columns 3 and 4 the average increase in swelling of the injected paw, column 3 being days 0 to 10 and column 4, being days 10–16; columns 5 and 6 the average increase in swelling of the uninjected paw, column 5 being days 0 to 10 and column 6 being days 10–16; columns 7 and 8 give the percent inhibition of swelling, column 7 for the injected paw at day 16, and column 8 for the uninjected paw for day 16. The p value is given directly beneath a particular determination in these latter columns.

A similar determination was made of the combined effect of vinblastine and an anti-inflammatory drug such as phenoprofen in the treatment of adjuvant arthritis. The arthritis was induced as before but phenoprofen as the calcium salt was given for six days—days 10–15—while vinblastine was, as before, given only on the 10th day after injection. Separate determinations of the effects of these drugs were made as well as their combined effect. Table 1, in Section B gives the results of these assays.

TABLE 1

SECTION A

| Name of Drug | Dose mg/kg | Average Increase in Swelling | | | | Percent Inhibition Swelling | |
|---|---|---|---|---|---|---|---|
| | | Injected Paw | | Uninjected Paw | | Infected Paw | Uninjected Paw |
| | | Day 0–10 | Day 10–16 | Day 0–10 | Day 10–16 | | |
| Saline Control | | 0.507 | 1.175 | 0.089 | 0.570 | | |
| Vinblastine Sulfate | 3 | 0.554 | 0.722 | 0.024 | 0.574 | 38.55 p = 0.097 | 0 p = 0.987 |
| Vinblastine Sulfate | 6 | 0.498 | 0.188 | 0.038 | 0.146 | 84.00 p = 0.001 | 74.39 p = 0.077 |
| Vinblastine Sulfate | 9 | 0.492 | −0.096* | 0.230 | −0.232* | 100.0 p = 0.000 | 100.00 p = 0.004 |
| Vinblastine Sulfate | 12 | 0.698 | −0.108* | −0.102* | −0.048* | 100.00 p = 0.000 | 100.00 p = 0.027 |

TABLE 1

SECTION B

| Name of Drug | Dose mg/kg | Average Increase in Swelling | | | | Percent Inhibition Swelling | |
|---|---|---|---|---|---|---|---|
| | | Injected Paw | | Uninjected Paw | | Infected Paw | Uninjected Paw |
| | | Day 0–10 | Day 10–16 | Day 0–10 | Day 10–16 | | |
| Saline Control | | 0.507 | 1.175 | 0.089 | 0.570 | | |
| Fenoprofen | 5 | 0.502 | 0.692 | 0.188 | 0.274 | 41.11 | 51.93 |

TABLE 1-continued

SECTION B

| Name of Drug | Dose mg/kg | Average Increase in Swelling | | | | Percent Inhibition Swelling | |
|---|---|---|---|---|---|---|---|
| | | Injected Paw | | Uninjected Paw | | Infected Paw | Uninjected Paw |
| | | Day 0-10 | Day 10-16 | Day 0-10 | Day 10-16 | | |
| (Ca salt) Vinblastine sulfate | 6 | 0.498 | 0.188 | 0.030 | 0.146 | $p = 0.074$ 84.00 $p = 0.001$ | $p = 0.282$ 74.39 $p = 0.077$ |
| Fenoprofen (Ca salt) Vinblastine Sulfate | 5 6 | 0.570 | −0.020* | 0.165 | −0.068* | 100.00 $p = 0.001$ | 100.00 $p = 0.022$ |

*Indicates a decrease in parameter from previous value.

Similar experiments were carried out with vinblastine-fenoprofen combinations and a vinblastine-indomethacin combination, again using adjuvant arthritis as a model. In this first determination, vinblastine was, as before, given on the 10th day, but fenoprofen, as the calcium salt, was given both from day 0 through day 15 and from day 10 through day 15. Controls utilizing each drug alone were employed as well as a saline control. Table 2 summarizes the results of this experiment. In addition, weight loss in grams for both protocols are given in the last column in the table. In the vinblastine-indomethacin experiment, vinblastine was given on day 11 and indomethacin daily from days 11 to day 16. Table 3 gives the results of this experiment, again using vinblastine alone, indomethacin alone, the combination and a saline control.

TABLE 2

| Name of Drug | Dose mg/kg | Day(s) | PERCENT INHIBITION OF SWELLING | | WT. LOSS IN GRAMS | |
|---|---|---|---|---|---|---|
| | | | Injected Paw | Uninjected Paw | Day 10-16 | Day 0-16 |
| Vinblastine sulfate | 3 | 10 | 8.22 $p = 0.724$ | 12.0 $p = 0.764$ | −22.6 | −22.3 |
| Fenoprofen* Ca Salt | 2.5 | 0-15 | 34.9 $p = 0.196$ | 17.4 $p = 0.645$ | −15.6 | −26.4 |
| Fenoprofen plus vinblastine sulfate | 2.5 3 | 10-15 10 | 44.5 $p = 0.037$ | 49.80 $p = 0.171$ | −15.2 | −24.6 |
| Fenoprofen Ca salt | 5 | 10-15 | 40.3 $p = 0.58$ | 27.2 $p = 0.385$ | −21.68 | −25.9 |
| Fenoprofen Ca salt vinblastine sulfate | 5 3 | 10-15 10 | 41.2 $p = 0.113$ | 62.01 p 0.073 | −11.51 | −8.5 |
| Saline Control | | | | | −13.5 | −20.6 |

*one death at day 16

TABLE 3

| Name of Drug | Dose mg/kg | Day(s) | INHIBITION OF SWELLING MEAN DIFFERENCE | | WT. LOSS IN GRAMS |
|---|---|---|---|---|---|
| | | | Injected Paw | Uninjected Paw | Day 10-17 |
| Vinblastine sulfate | 3 | 10 | 1.00 $p = 1$ | 0.41 $p = 1$ | 28.9 |
| Indomethacin | 0.25 | 10 | 0.59 $p = 0.11$ | 0.56 $p = 1$ | |
| Vinblastine sulfate plus Indomethacin | 3 0.25 | 10 | 0.43 $p = .001$ | 0.23 $p = 067$ | 28.8 |
| Control | — | 10 | 1.26 | 0.69 | 30.6 |

Vinblastine is also active in other assays designed to detect anti-arthritic activity as, for example, the twine granuloma assay in female rats.

As can be seen from the above data, vinblastine sulfate and fenoprofen calcium salt or indomethacin in combination are effective in inhibiting induced arthritis at dose levels at which neither drug alone is effective. In addition, weight loss, as a measure of toxicity, was less for the protocol calling for one injection of vinblastine at day 10 and fenoprofen orally only on days 10-15 than for either above. This protocol corresponds closely to an actual treatment pattern for mammalian arthritis.

In combination, the effective dosages of vinblastine and fenoprofen or of vinblastine and indomethacin for treating arthritis are in general lower than those routinely used with either drug alone; i.e., 0.1–0.5 mg/kg for vinblastine sulfate and 8–10 mg/kg 4 times a day for fenoprofen calcium salt. I prefer to employ in my novel treatment method a single I.V. dosage in the range of 0.05–0.3 mg/kg (1.85–11.1 mg/M$^2$) for vinblastine sulfate and a continuing oral dosage of 48 mg/kg 4 times a day (daily total = 16–32 mg/kg) for fenoprofen calcium salt. Again, if vinblastine or other equivalent vinca alkaloid is administered by the oral route, the dose level will be about 10 times the I.V. vinblastine dosage.

The above drug combinations are best administered as follows: vinblastine or its equivalent is administered when the rheumatoid arthritis is first diagnosed; and thereafter, as necessary, not more often than biweekly or monthly. Simultaneously, administration of the profen-type anti-inflammatory agent or of indomethacin is begun and continued on a daily basis at a dose equivalent to 4–6 mg/kg 4 times a day of fenoprofen or 25–50 mg three times a day for indomethacin. The dose level of this drug is usually reduced after the initial dosage to the lowest compatible with relief of pain. The drugs are thus administered separately and only initially more or less simultaneously.

Since it has been shown by the above assays that vinblastine is active in the adjuvant arthritis assay and therefore useful in the treatment of rheumatoid arthritis. It is apparent that other diseases involving the same cell types as those affected in the animal models of adjuvant arthritis would also be favorably treated by the use of vinblastine. These diseases include atherosclerosis in which there is a proliferation of fibroblasts to form an aetheroma, graft rejection involving the suppression of macrophages and lymphocytes, diseases involving excessive collagen production and/or fibrocycial formation including scleroderma, idiopathic pulmonary fibrosis, etc.

I claim:

1. A method of treating rheumatoid arthritis in mammals which comprises administering to a mammalian subject suffering from rheumatoid arthritis and in need of treatment, an anti-arthritically-effective dosage of a vinca-derived oncolytic agent from the group consisting of vinblastine, vindesine, vincristine, 1-4′-deoxyleurosidine, 4′-deoxyleurosidine, 4-desacetyl VLB 3″-(β-chloroethyl)-3-spiro-5″-oxazolidine-2″,4″-dione and 4-desacetyl VLB 3″-methyl-3-spiro-5″-oxazolidine-2″,4″-dione.

2. A method according to claim 1 in which the vinca-derived oncolytic agent is vinblastine.

3. A method according to claim 1 in which the vinca-derived oncolytic agent is administered by the intravenous route.

4. A method according to claim 3 in which the dosage of vinca-derived oncolytic agent is equivalent to 0.1–0.5 mg/kg of vinblastine.

5. A method according to claim 1 in which the vinca-derived oncolytic agent is administered orally.

6. A method according to claim 5 in which the oral dosage of the vinca-derived oncolytic agent is equivalent to 1–5 mg/kg of vinblastine administered orally.

7. A method of treating rheumatoid arthritis in mammals which comprises administering to a mammalian subject suffering from rheumatoid arthritis and in need of treatment, single, spaced antiarthritically effective doses of vinblastine in conjunction with continuing daily anti-inflammatorially-effective doses of a profen-type anti-inflammatory agent.

8. A method according to claim 7 in which the vinblastine is administered by the intravenous route at a dose in the range 0.5–0.3 mg/kg.

9. A method according to claim 7 in which the profen-type agent is fenoprofen.

10. A method according to claim 9 in which the daily fenoprofen dosage is in the range 16–32 mg/kg per day.

11. A method of treating rheumatoid arthritis in mammals which comprises administering to a mammalian subject suffering from rheumatoid arthritis and in need of treatment, single, spaced antiarthritically effective doses of vinblastine in conjunction with continuing daily anti-inflammatorially-effective doses of indomethacin.

12. A method according to claim 11 in which the vinblastine is administered by the intravenous route at a dose in the range 0.5–0.3 mg/kg.

13. A method according to claim 11 in which the daily indomethacin dosage is in the range 75–150 mg.

* * * * *